US008899979B2

(12) United States Patent
Anderson et al.

(10) Patent No.: US 8,899,979 B2
(45) Date of Patent: Dec. 2, 2014

(54) MATRIX RING FOR TOOTH RESTORATION

(71) Applicant: Garrison Dental Solutions, Spring Lake, MI (US)

(72) Inventors: Robert Anderson, Coopersville, MI (US); Scott Doenges, West Olive, MI (US); Alex Hull, Hudsonville, MI (US)

(73) Assignee: Garrison Dental Solutions, Spring Lake, MI (US)

( * ) Notice: Subject to any disclaimer, the term of this patent is extended or adjusted under 35 U.S.C. 154(b) by 76 days.

(21) Appl. No.: 13/781,252

(22) Filed: Feb. 28, 2013

(65) Prior Publication Data

US 2014/0242544 A1     Aug. 28, 2014

(51) Int. Cl.
*A61C 7/00*     (2006.01)
*A61C 5/12*     (2006.01)

(52) U.S. Cl.
CPC ..................................... *A61C 5/125* (2013.01)
USPC ......................................................... 433/148

(58) Field of Classification Search
USPC ........... 433/39, 135, 137, 138, 148, 149, 150, 433/153, 155, 156, 162; 606/156, 157, 158
See application file for complete search history.

(56) References Cited

U.S. PATENT DOCUMENTS

| | | | | |
|---|---|---|---|---|
| 5,607,302 A * | 3/1997 | Garrison et al. | ................. | 433/39 |
| 5,697,942 A * | 12/1997 | Palti | ............................. | 606/151 |
| 6,206,697 B1 * | 3/2001 | Hugo | ............................. | 433/155 |
| 6,589,053 B2 * | 7/2003 | Bills | ............................. | 433/139 |
| 7,175,432 B2 * | 2/2007 | McDonald | .................... | 433/153 |
| 7,284,983 B2 * | 10/2007 | McDonald | .................... | 433/153 |
| 7,367,937 B2 * | 5/2008 | Jambor et al. | ................... | 600/37 |
| 7,909,839 B2 * | 3/2011 | Fields | ............................. | 606/157 |
| 8,029,281 B2 * | 10/2011 | Ho | .................................... | 433/148 |
| 2002/0155410 A1 * | 10/2002 | Bills | ............................. | 433/153 |
| 2003/0059741 A1 | 3/2003 | Bills | | |
| 2003/0148245 A1 * | 8/2003 | Anderson | ...................... | 433/148 |

(Continued)

FOREIGN PATENT DOCUMENTS

FR     002555952 A1 *     6/1985

OTHER PUBLICATIONS

PCT International Search Report regarding Application No. PCT/US2014/018643 filed Feb. 26, 2014, a counterpart to U.S. Appl. No. 13/781,252.

(Continued)

*Primary Examiner* — Cris L Rodriguez
*Assistant Examiner* — Mirayda A Aponte
(74) *Attorney, Agent, or Firm* — Warner Norcross & Judd LLP (57) ABSTRACT

A matrix ring includes a biasing ring and a pair of opposing tines. The biasing ring includes a substantially hoop-like configuration terminating at two opposing ends. The pair of opposing tines extend inwardly from each of the two ends of the biasing ring toward each other. Each of the pair of opposing tines is coupled to the respective opposing end about a central region thereof and extends radially outwardly therefrom. Each tine includes a flame body having a central ridge and opposing lower extensions, the lower extensions terminating at an exposed face. The portion of the lower extensions proximate the exposed face being able to move relative to the rest of the flame body so as to better position on the teeth of a patient. A superimposed pad over portions of the flame body provides a deformable surface for engagement with the surface of the tooth of a patient.

16 Claims, 7 Drawing Sheets

(56) References Cited

U.S. PATENT DOCUMENTS

| | | | |
|---|---|---|---|
| 2004/0267292 A1* | 12/2004 | Byrum et al. | 606/157 |
| 2005/0118554 A1* | 6/2005 | Kilcher et al. | 433/141 |
| 2005/0147941 A1 | 7/2005 | McDonald | |
| 2007/0016231 A1* | 1/2007 | Jambor et al. | 606/157 |
| 2007/0172793 A1* | 7/2007 | Doenges et al. | 433/139 |
| 2008/0064004 A1* | 3/2008 | Clark | 433/39 |
| 2008/0064009 A1* | 3/2008 | Clark | 433/148 |
| 2009/0208901 A1 | 8/2009 | Doenges et al. | |
| 2011/0311945 A1* | 12/2011 | Bertolotti et al. | 433/139 |
| 2012/0164594 A1* | 6/2012 | Pieroni et al. | 433/39 |
| 2013/0004914 A1* | 1/2013 | Marteney et al. | 433/149 |
| 2013/0226200 A1* | 8/2013 | Kappel et al. | 606/142 |

OTHER PUBLICATIONS

PCT International Written Opinion regarding Application No. PCT/US2014/018643 filed Feb. 26, 2014, a counterpart to U.S. Appl. No. 13/781,252.

* cited by examiner

MATRIX RING FOR TOOTH RESTORATION

BACKGROUND OF THE DISCLOSURE

1. Field of the Disclosure

The invention relates in general to dental implements, and more particularly, to a matrix ring which is used to separate teeth and to hold a matrix band in place around a tooth when a cavity in the tooth is to be filled or otherwise repaired or restored.

2. Background Art

The use of retaining devices for holding matrix bands is well known in the art. Typically, when tooth decay occurs near the outer edges of a tooth, there is often insufficient tooth structure remaining to support the filling material prior to hardening thereof. To overcome this problem, a thin band is positioned about the tooth and secured to the tooth to provide the required support for the filling material. In such a manner, the filling material can be positioned as desired, and can be formed into the desired shape.

To achieve the proper final desired shape, it is often necessary to separate the affected tooth from the immediately adjacent teeth. This is typically accomplished through the use of open ended rings having downwardly projecting tines, the ends of which are placed on opposing sides of the region between the affected tooth and an adjacent tooth which requires separation. Use of such a device requires the separation of the opposing tines positioned at the ends of the open ended rings, and the positioning of the respective tines on opposing sides of the teeth. When released, the spring like nature of the ring provides an inward force against the tines which drives the tines toward each other. In turn, the teeth positioned between the tines generally are forced away from each other thereby increasing the interproximal space between the two teeth.

Over the years, improvements have been made so that the tines of the matrix ring more closely follow the contours of the teeth. Additionally, improvements have been made that have positively impacted the placement, movement, and adjustment of matrix rings. Other improvements have led to an expansion of the range of teeth to which a single matrix ring can adapt. Despite these improvements, there has been a need to still further improve the configuration of matrix rings, and the tines of matrix rings, to address the shortcomings in the art.

SUMMARY OF THE DISCLOSURE

The disclosure is directed to a matrix ring. The matrix ring has a biasing ring, and a pair of opposing tines. The biasing ring has a substantially hoop-like configuration terminating at two opposing ends which are spaced apart from each other a distance. The pair of opposing tines extend inwardly from each of the two ends of the biasing ring toward each other.

At least one of the tines, and preferably both of the opposing tines having a frame body and a superimposed pad. The frame body includes a front defined by a central ridge, a first lower extension extending from a first side of the central ridge, and a second lower extension extending from a second side of the central ridge. The first lower extension has a top surface and a bottom surface terminating at an exposed face. The top surface and bottom surface cooperate to define a thickness that reduces toward the exposed face. A portion of the first lower extension proximate the exposed face is configured to rotate and translate relative to the remainder of the frame body upon application of an operable positioning within a mouth of a patient. The second lower extension has a top surface and a bottom surface terminating at an exposed face. The top surface and bottom surface cooperate to define a thickness that reduces toward the exposed face. A portion of the second lower extension proximate the exposed face is configured to rotate and translate relative to the remainder of the frame body upon operable positioning within a mouth of a patient. The exposed faces of each of the first and second lower extensions being spaced apart from each other and configured for independent relative movement.

The superimposed pad is positioned over a portion of the front of the frame body. The superimposed pad has a first side and a second side. The first side extends over the top surface of the first lower extension and extends to the central ridge. The second side extends over the top surface of the second lower extension and extends to the central ridge. The superimposed pad has a first front face and a second front face, which together with the central ridge and the exposed faces of the first and second lower extensions defines the tooth engagement surface of the tine. The superimposed pad comprising an elastic material configured to elastically deform upon operable positioning within the mouth of a patient, or upon relative movement of the first and second lower extensions.

In a preferred embodiment, the second tine is a substantial mirror image of the first tine about an axis that is positioned substantially midway between the opposing ends of the biasing ring.

In another preferred embodiment, the first and second front faces of each of the superimposed pads of each of the first and second tines are outwardly and upwardly concave.

In another preferred embodiment, the exposed face of the first lower extension further includes an inclined face relative to the bottom surface of the first lower extension. The exposed face includes an upper edge and a lower edge, with a projecting edge spaced apart from the upper edge. The projecting edge extends further toward the opposing tine than the remainder of the exposed face.

In a preferred embodiment, the inclined face of the first lower extension is inclined at an angle of between 25° and 75° relative to the bottom surface of the first lower extension.

In another preferred embodiment, the exposed face of the second lower extension further includes an inclined face relative to the bottom surface of the second lower extension having an upper edge and a lower edge. A projecting edge is spaced apart from the upper edge. The projecting edge extends further toward the opposing tine than the remainder of the exposed face.

In a preferred embodiment, the inclined face of the first and second lower extensions is configured to rotate relative to the remainder of the frame body at least 10° of rotation in either direction about an axis that extends through the respective exposed face.

In a preferred embodiment, the projecting edge of each of the exposed faces of the first and second lower extensions correspond to the respective lower edge thereof.

Preferably, the exposed face of each of the first and second lower extension is spaced apart from the front face of the respective superimposed pad so as to define a projecting edge therebetween.

In another preferred embodiment, the top surface and the bottom surface of the first lower extension is substantially continuous with the space therebetween tapering toward the exposed face.

In another preferred embodiment, the superimposed pad includes at least one crossover portion extending through the central ridge that links the superimposed pad on either side of the central ridge. More preferably, a pair of spaced apart crossover portions extend through the central ridge linking the superimposed pad on either side of the central ridge.

In another preferred embodiment, the opposing ends of the biasing ring terminate within opposing cavities of the respective opposing tines.

Preferably, the superimposed pad comprises a silicone, and the frame body comprises a polyether ether ketone (PEEK).

In another preferred embodiment, the central ridge includes an exposed face having a peak, a first side and a second side on an opposite side of the peak from the first side. The first side is substantially continuous with the first surface of the superimposed pad. The second side is substantially continuous with the second surface of the superimposed pad.

In another preferred embodiment, the central ridge is outwardly concave between an upper and lower end thereof.

BRIEF DESCRIPTION OF THE DRAWINGS

The disclosure will now be described with reference to the drawings wherein.

DETAILED DESCRIPTION OF THE DISCLOSURE

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Figure 1:
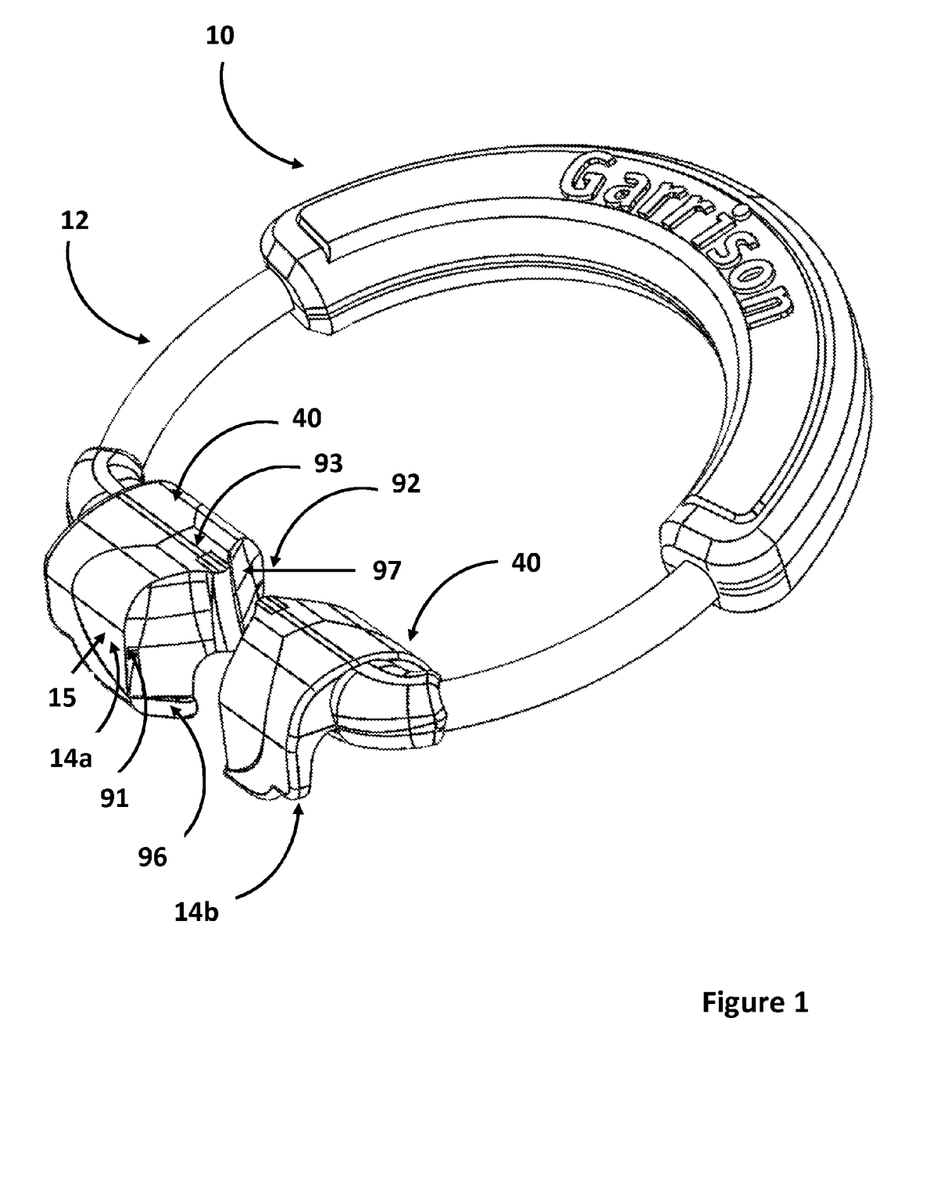
FIG. 1 of the drawings is a perspective view of the matrix ring of the present disclosure.

Referring now to the drawings and in particular to FIG. 1, the dental implement, or matrix ring, is shown generally at 10. The matrix ring 10 includes biasing ring 12 and opposing tines 14a, 14b. The dental implement is typically configured for separating adjoining teeth and for retaining a band or matrix against a tooth undergoing repair. One such band is disclosed in U.S. Pat. App. Pub. No. 2011/0070555 A1 published to Anderson et al., the entire disclosure of which is hereby incorporated by reference in its entirety. Of course, the matrix band disclosed in this publication is not to be deemed limiting, but rather deemed as being exemplary of the bands with which the matrix ring can be utilized. The matrix band of the present disclosure is configured for use in association with any number of different matrix bands, and is not limited to use with any particular one or type of matrix bands. Another band configuration, and matrix ring, is shown in U.S. Pat. No. 5,607,302 issued to Garrison et al, the entire disclosure of which is hereby incorporated by reference in its entirety.

More particularly, the opposing tines 14a, 14b press against the interproximal space between the two adjoining teeth and against the teeth themselves to provide a structure for the tooth undergoing repair. The dentist or dental practitioner can secure and shape the band with the dental implement and then fill the formed volume with a filler product.

Figure 2:
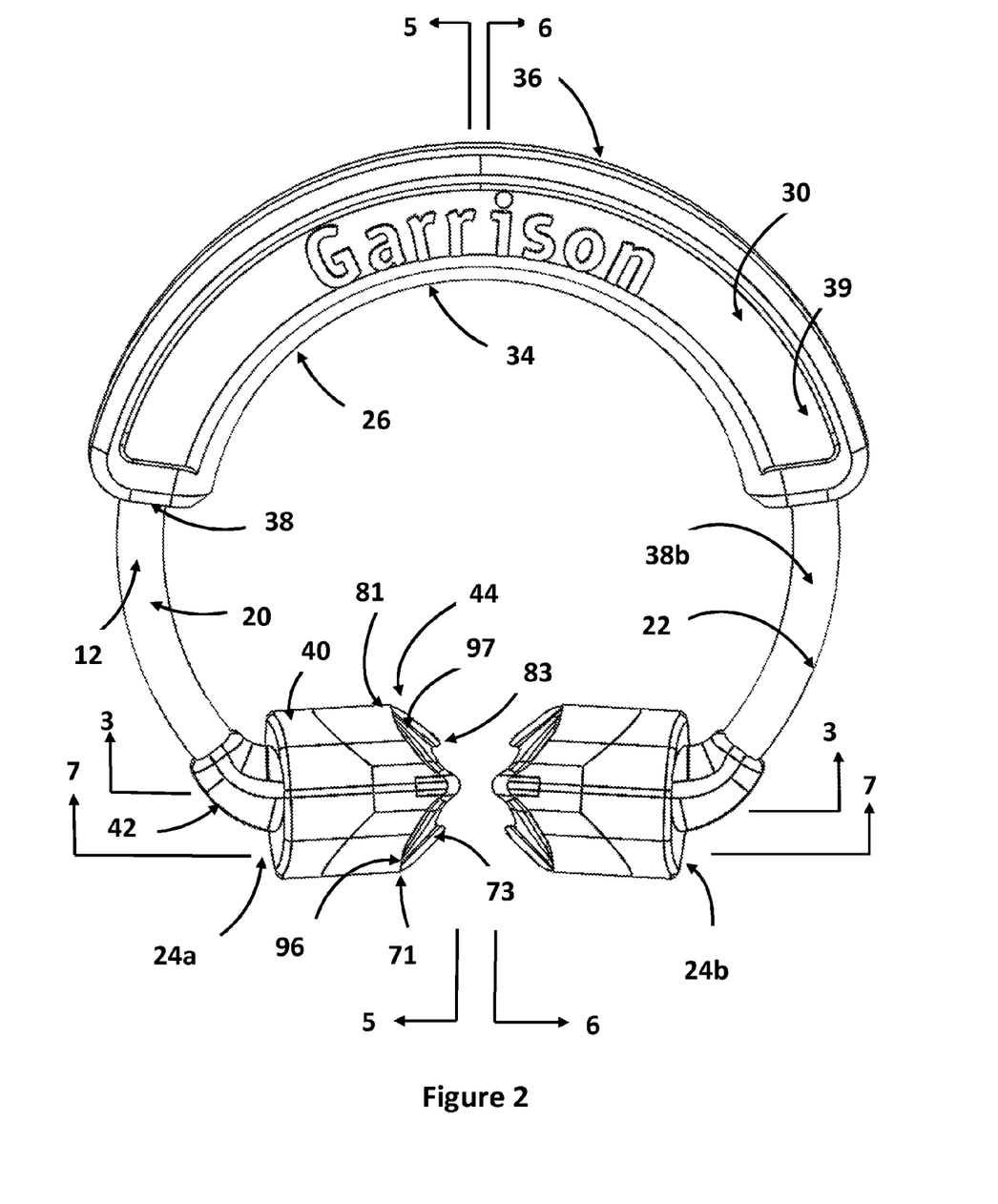
FIG. 2 of the drawings is a top plan view of the matrix ring of the present disclosure.

With reference to FIG. 2, the biasing ring 12 comprises body 20 which comprises a hoop-like member having two opposing ends, a first opposing end 24a and second opposing end 24b. The two ends are configured so as to substantially face each other, separated by a distance from each other. The biasing ring additionally includes a cross-sectional configuration and an outer surface 22. The embodiment contemplated comprises a substantially circular hoop-like configuration, with a substantially circular cross-sectional configuration made from a stainless steel spring wire (whereas it is also contemplated that other materials may be utilized, including other metals and alloys, as well as polymers, such as, but not limited to, a polyether ether ketone (PEEK)). In other embodiments the hoop-like configuration may comprise a square hoop-like configuration, an elliptical hoop-like configuration, a hexagonal hoop-like configuration, arbitrary hoop-like configurations.

The biasing ring further may include secondary ring 26 which is molded over a portion of the biasing ring. With combined reference to FIGS. 2 and 9, the secondary ring includes a top surface 30, bottom surface 32, outside surface 34, inside surface 36. The secondary ring 26 comprises, preferably, a rigid polymer that is molded onto the biasing ring. Polymers that are contemplated comprise a polyether ether ketone (PEEK), polypropylene, polyethylene and/or nylon material among others. The secondary ring extends about a portion of the hoop-like configuration terminating at first end 38a and second end 38b. In the embodiment shown, the secondary ring extends over approximately half of the hoop-like configuration. Additionally, the top and bottom surfaces are thinnest at the ends and thickest at an end opposite of the opposing ends 24a, 24b of the body. Of course, the dimensions and the relative widths and thicknesses can be varied within the scope of the invention.

Figure 9:
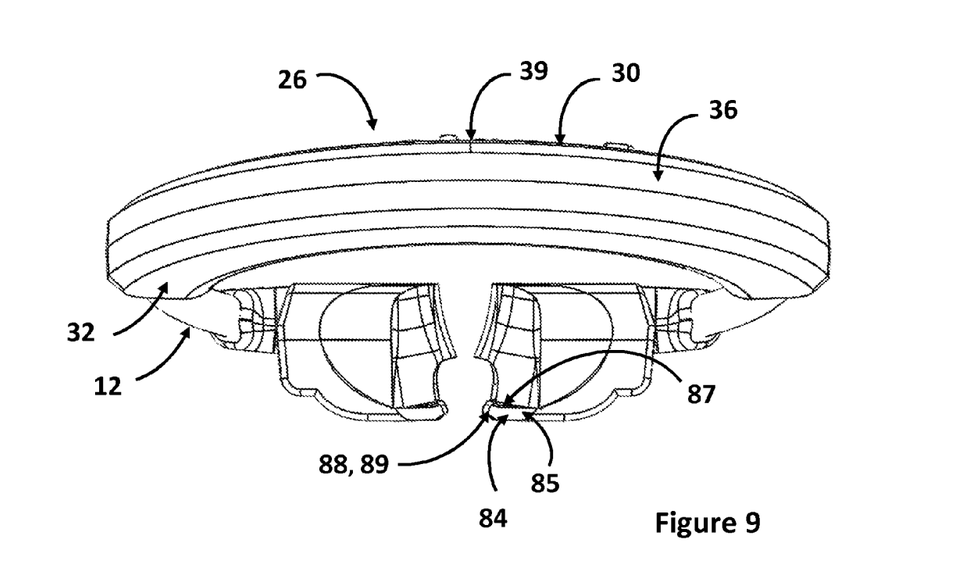
FIG. 9 of the drawings is a back elevational view of the matrix ring of the present disclosure.

The secondary ring 26 may further include an over-mold gripping region 39 which extends over a portion of the top surface 30, and inside surface 36 of the secondary ring 26. The over-mold gripping region 39 generally comprises a silicone material which is substantially softer than the surrounding rigid polymer biasing ring. Of course other relatively resilient polymers, such as elastomers or such and rubber, are likewise contemplated for use. It will further be understood that the secondary ring 26 may comprise a singular material that is of the requisite rigidity such that the over-mold gripping region 39 is not necessary. In still other embodiments it may be advantageous to provide other configurations of the ring, other profiles of the ring as well as other configurations that require multiple different components and/or materials.

The opposing tines 14a, 14b are shown in FIG. 1. The opposing tines in the preferred embodiment are substantial mirror images of each other about a vertical plane substantial positioned between the interproximal space of the opposing tines. As a result, the opposing tine 14a will be described with the understanding that the opposing tine 14b is a 20 substantial mirror image thereof. To the extent that any structures are identified on the opposing tine 14b with reference numbers, these structures are denoted with the same reference number as on the opposing tine 14a.

Figure 3:
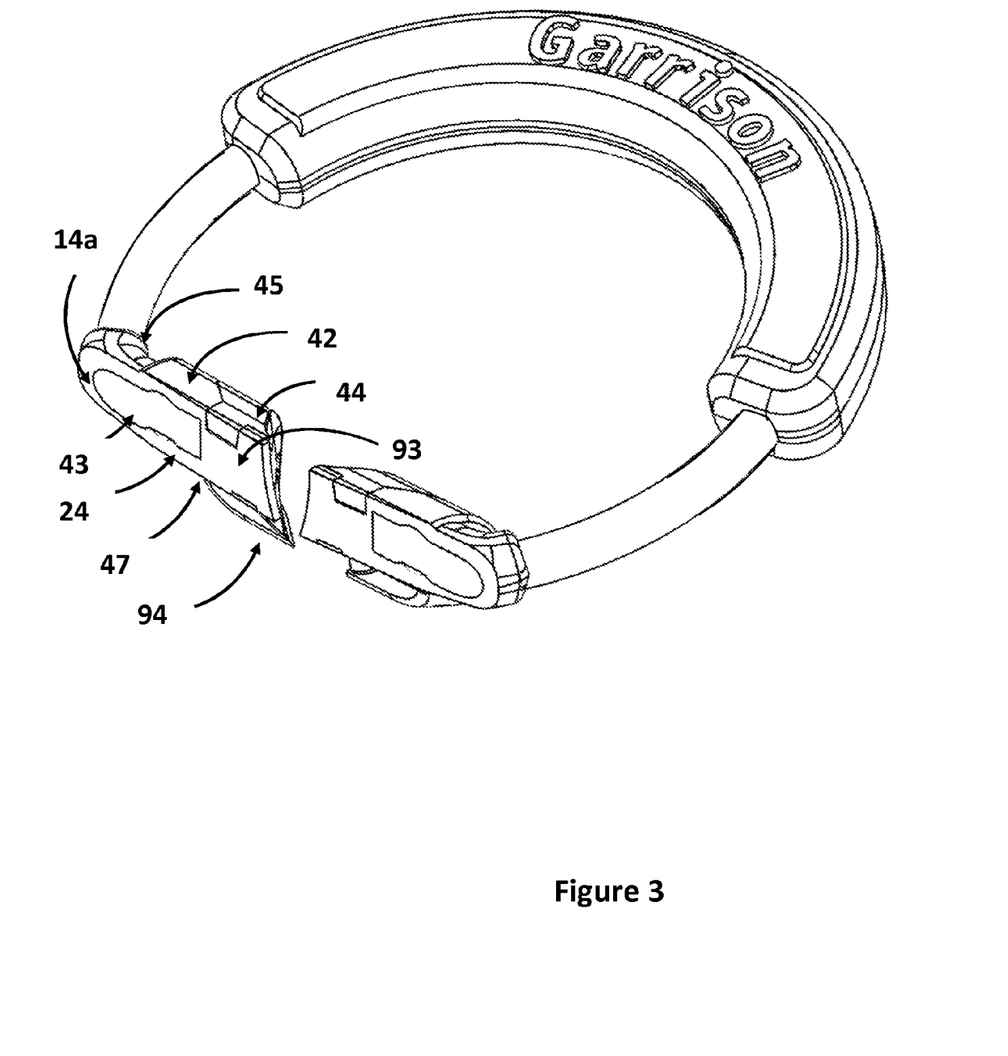
FIG. 3 of the drawings is a perspective cross-sectional view of the matrix ring of the present disclosure, showing, in particular, the internal portions of the tines, taken generally about lines 3-3 of FIG. 2.

With reference to FIGS. 1 and 2, the opposing tine 14a comprises frame body 40, which includes back 42 and front 44. With reference to FIG. 3, the back includes collar 43 which defines opening 45 which is in communication with the cavity 47. As will be understood, the first end 24a of the biasing ring 12 extends into the opening of the collar and into the cavity. In the embodiment shown, the opposing tine 14a is molded over the first end 24a of the biasing ring. The frame body 40 is preferably formed from a single integrally molded polymer member, such as a polyether ether ketone (PEEK), or, a polysulphone (PPSU), such as PPSU sold under the trademark Radel® available from Solvay Plastics. Of course other materials are likewise contemplated for use, including, but not limited to, composites as well as metals and alloys thereof. Preferably, the relatively rigid frame provides a hardness and an overall structure to the tine. As is set forth below, however, it will be understood that, due to the configuration and dimensions of the first and second lower extensions, the material from which the rigid frame is made has a degree of flexibility associated therewith. It will also be understood that in other embodiments the rigid frame 40 may comprise a plurality of different components that are coupled together through welding, adhesion or other joining systems.

Figure 4:
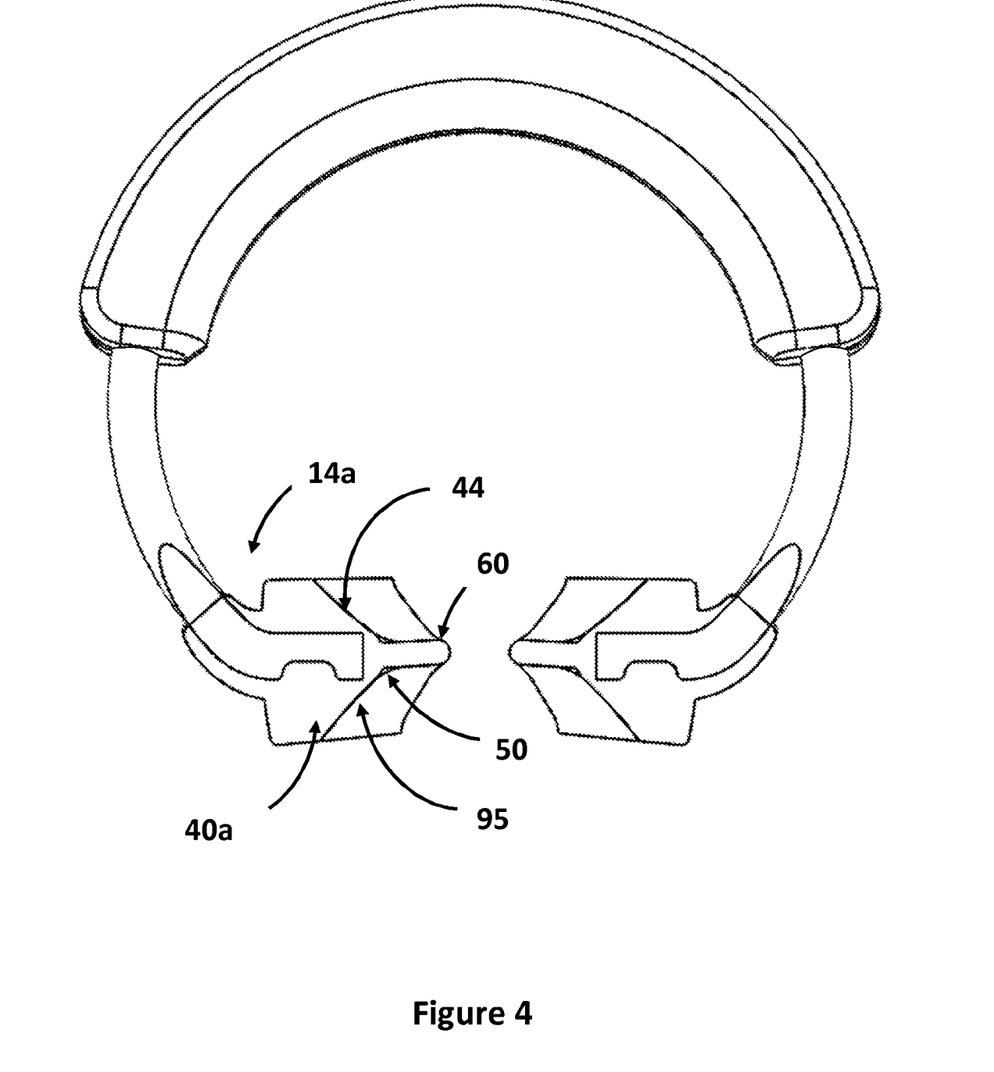
FIG. 4 of the drawings is a cross-sectional view of the matrix ring of the present disclosure, showing, in particular, the internal portions of the tines, taken generally about lines 4-4 of FIG. 8.
Figure 5:
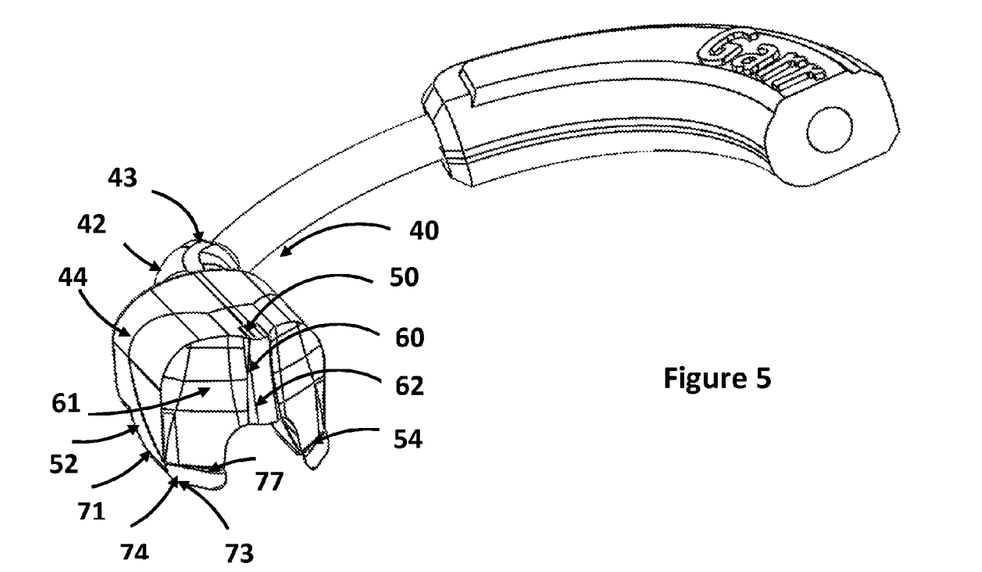
FIG. 5 of the drawings is a partial cross-sectional view of the matrix ring of the present disclosure, taken generally about lines 5-5 of FIG. 2.
Figure 6:
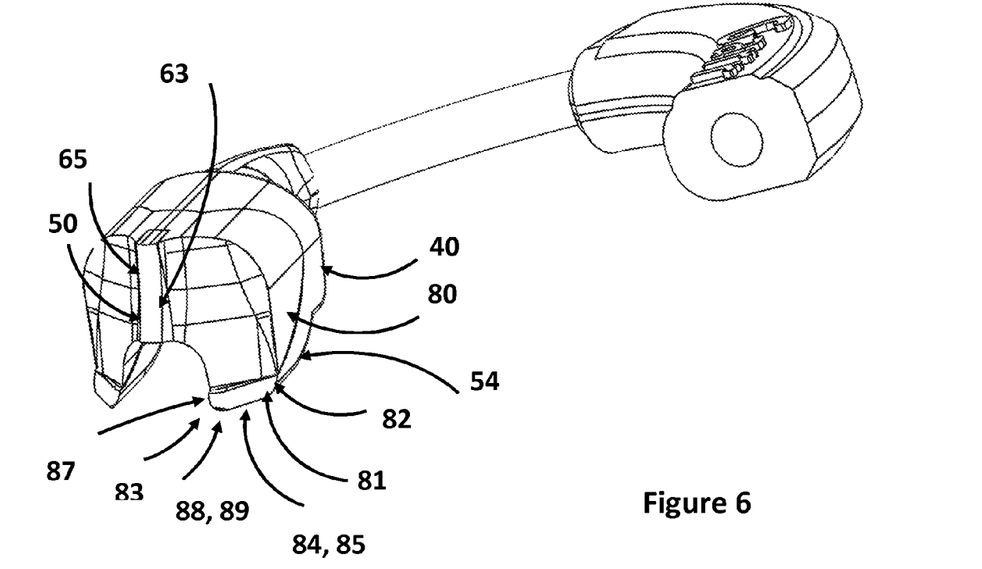
FIG. 6 of the drawings is a partial cross-sectional view of the matrix ring of the present disclosure, taken generally about lines 6-6 of FIG. 2.

With reference to FIGS. 4, 5 and 6, the front 44 is shown as comprising a topography defined by central ridge 50, first lower extension 52 and second lower extension 54. The central ridge 50 extends outwardly toward the opposing tine 14b, and includes distal end 60. The distal end 60 defines exposed face 62. It will be understood that the exposed face 62 is a portion of the tooth contact region, such that, the exposed face may come into contact with teeth of the patient, or may be in the interproximal space thereof. The exposed face includes first side 61 and second side 63, which meet at peak region 65. The peak region 65 may comprise a peak (i.e., a sharp continuous line or a continuous curved region), or may comprise a surface which is generally oblique to either one of the sides 61, 63. It is contemplated that in other embodiments the central ridge may be completely covered by the superimposed pad such that there is no exposed face 62. That is, the distal end 60 is covered by the superimposed pad, and, in turn, no portion of the central ridge forms the outward face of the respective tine.

Figure 7:
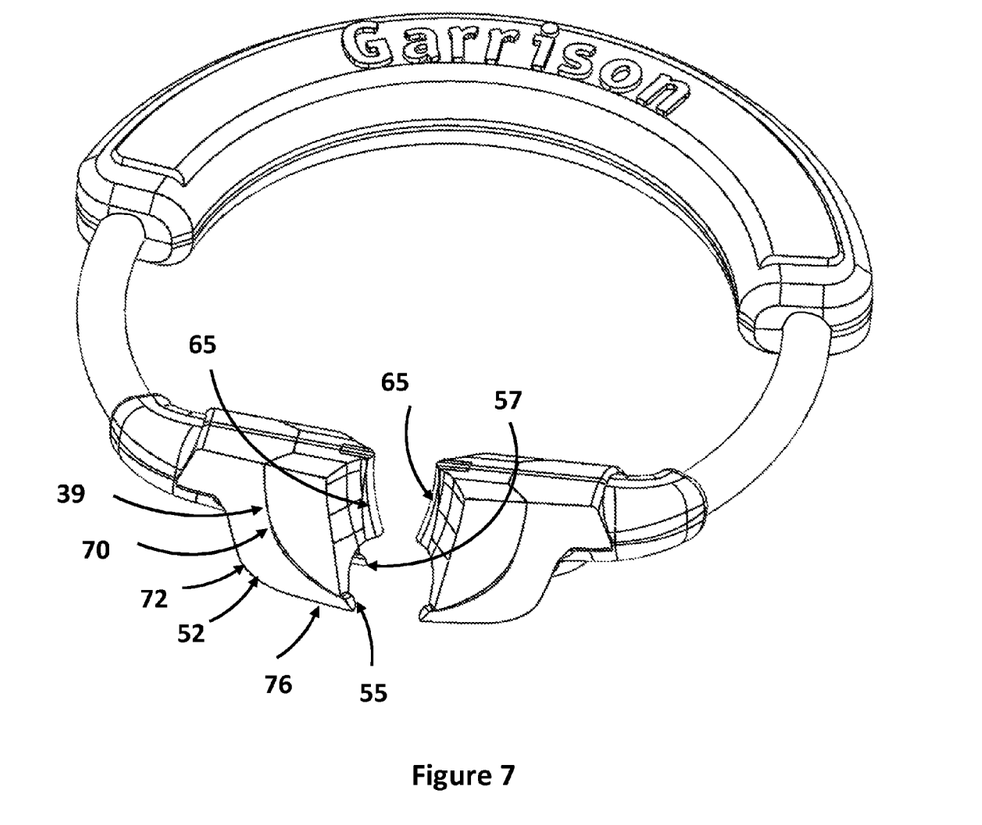
FIG. 7 of the drawings is a partial cross-sectional view of the matrix ring of the present disclosure, taken generally about lines 7-7 of FIG. 2.

With reference to FIGS. 5 and 7, the first lower extension 52 extends outwardly from the rigid frame body on one side of the central ridge 50. The first lower extension includes top surface 70, bottom surface 72, and sides 71, 73. The first lower extension tapers toward the distal end 76 thereof such that the thickness of the first lower extension decreases toward the distal end (in the embodiment shown, the top surface and the bottom surface are both curved, with the upper surface being a more drastically sloped curve, which places the two surfaces closer to each other toward the distal end). With the material that is utilized for the rigid frame body, at some point, the thickness is such that the distal end (and some portion spaced apart from the distal end) can flex up and down, and can twist relative to the remainder of the rigid frame body. It is contemplated that the flexing of the distal end is greater in the up and down direction than the thickness of the first lower extension proximate the distal end. It is also contemplated that the first lower extension may be able to rotate at least 10° about a point between the sides 71, 73 of the first lower extension in either one or both of the clockwise and counter-clockwise direction relative to an axis that extends through the exposed surface. It is also contemplated that the vertical distance that the distal end can move up or down may correspond to at least half of the thickness of the exposed face 74. This independent movement in multiple directions and manners (i.e., different degrees of freedom) facilitates the custom fit of the tine relative to the tooth, and facilitates the improved placement, and position retention of the tine relative to the teeth that are engaged.

Figure 8:
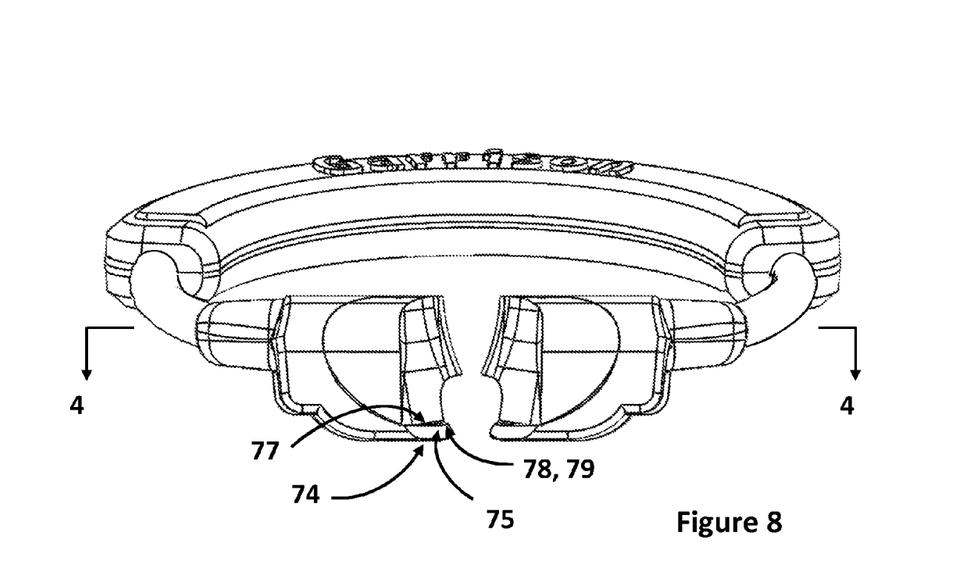
FIG. 8 of the drawings is a front elevational view of the matrix ring of the present disclosure.

With reference to FIGS. 5 and 8, collectively, the exposed face 74 comprises a generally inclined face 75 which includes a projecting edge 79. In the embodiment shown, the inclined face includes upper edge 77 and lower edge 78. The lower edge, in this embodiment comprises the projecting edge 79. In other embodiments, the projecting edge may be spaced apart a distance from the lower edge, toward the upper edge 77. It is preferred that the upper edge and the projecting edge be separated a distance so as to provide an inclined face 75. The edge, along with the inclined surface between the projecting edge 79 and the upper edge 77 provides a surface which, when the tine is in position, drives downwardly toward the gum line of the patient. In the embodiment shown, the front face is angled at approximately 60° relative to the bottom surface, and preferably, between 25° and 75°. In addition, the front face is substantially planar, although, non-planar configurations are likewise contemplated.

With reference to FIGS. 6 and 9, the second lower extension 54 extends outwardly from the rigid frame body on the opposite side of the central ridge 50 from the first lower extension 52. In many embodiments, the second lower extension is a substantial mirror image of the first lower extension, in principle. It will be understood, however, that the two may have differences in dimensions and locations, as well in performance. It will be understood that they can be tweaked relative to each other to achieve a desired configuration.

More specifically, the first lower extension includes top surface 80, bottom surface 82, and sides 81, 83. The second lower extension tapers toward the distal end thereof such that the thickness of the second lower extension decreases toward the distal end. With the material that is utilized for the rigid frame body, at some point, the thickness is such that the distal end (and some portion spaced apart from the distal end) can flex up and down, and can twist relative to the remainder of the rigid frame body. It is contemplated that the flexing of the distal end is greater in the up and down direction than the thickness of the first lower extension proximate the distal end. It is also contemplated that the second lower extension may be able to rotate at least 10° about a point between the sides 81, 83 of the first lower extension in either one or both of the clockwise and counter-clockwise direction relative to an axis that extends through the exposed surface. This independent movement facilitates the custom fit of the tine relative to the tooth, and facilitates the improved placement, and position retention of the tine relative to the teeth that are engaged.

The exposed face 84 comprises a generally inclined face 85 which includes a projecting edge 89. In the embodiment shown, the inclined face includes upper edge 87 and lower edge 88. The lower edge, in this embodiment comprises the projecting edge 89. In other embodiments, the projecting edge may be spaced apart a distance from the lower edge, toward the upper edge 87. It is preferred that the upper edge and the projecting edge be separated a distance so as to provide an inclined face 85. The edge, along with the inclined surface between the projecting edge 78 and the upper edge 87 provides a surface which, when the tine is in position, drives downwardly toward and often past the gum line of the patient. In the embodiment shown, the front face is angled at approximately 60° relative to the bottom surface, and preferably, between 25° and 75°. In addition, the front face is substantially planar, although, non-planar configurations are likewise contemplated. For example, lower edge (as well as a portion of the exposed face) may be curved such that it is outwardly concave, to, better match the shape of a tooth with which it will come into contact.

As will be explained below with respect to the operation, the exposed face of each of the lower extensions, and the projecting edge, defines a barb. Stated another way, these structures form a spade-like shape such that they drive subgingivally where they can engage the undercut region of the infrabulge. The inward force on the spade-like shape causes it to retain on the teeth even without the curvature of an infrabulge on the tooth. Furthermore, the flexibility of the lower extensions provides the ability to position the exposed faces such that the proper tooth contact can be achieved of each of the lower extensions relatively independently of each other.

It will be understood that due to the location of the exposed faces of the lower extensions, as well as their configuration, any slipping of the matrix ring causes further movement down the tooth rather than up the tooth to the occlusal surface. Furthermore these projecting edges act as a positive stop to ensure that the central ridge does not tend to locate too far interproximally. In the case of wide embrasures, the exposed faces of the lower extensions prevents the same from entering the proximal box where they can cave in the matrix band.

As can be seen in FIGS. 4 through 7, the front 44, including the central ridge (on either side thereof) as well as the lower extensions 52, 54 together define a generally outwardly concave surface configuration on either side of the central ridge. As will be explained, the superimposed pad is coupled to these generally outward concave surface configurations, and is defined as pad attachment surface 40a. It will be understood that the central ridge may include slots or the like extending between the opposing sides thereof, such that, when the superimposed pad is coupled thereto (through co-molding or the like), there appears to be a disconnect between the distal end 60 of the central ridge and the remainder of the rigid frame body 40. The configuration of the slots and the thickness of the central ridge as well as the placement of the slots can impart desirable characteristics to the central ridge relative to bending and rotating relative to the rest of the rigid frame body.

The superimposed pad 15 is shown in FIGS. 1, 2, 3 and 4 as comprising first side 91, second side 92, upper crossover portion 93 (FIG. 3), lower crossover portion 94 (FIG. 3), inner surface 95 (FIG. 4), first front face 96 and second front face 97. As can be seen, inner surface 95 is coupled to pad attachment surface 40a. With the slots that extend through the central ridge, the distal end of the central ridge appears to be separated from the remainder of the rigid frame body. Indeed, in certain embodiments, this may be the case, whereas in other embodiments, the connection may be fully visible to the dental professional. The first front face 96 and second front face 97 each comprise outwardly in upwardly concave surfaces that are generally configured to match or follow the contours of adjacent teeth. It will be understood that they may be substantial mirror images of each other about the central wedge or, they may be of different configuration.

The thickness of the superimposed pad is such that the shape that generally makes it provides a surface with both the opposing sides 61, 63 of the exposed face 62 of the central ridge. Additionally, the superimposed pad forms a surface with the exposed faces 74, 84 of the first lower extension and the second lower extension, respectively. These surfaces together define the engagement surface of the tine. It will be understood that it is this surface which engages the tooth and other tooth structures, as well as the matrix band (while it will be understood that the contact is not full, and portions of the engagement surface will be positioned in the interproximal space and not in direct contact with opposing teeth). The superimposed pad comprises an elastomeric member which may be molded over the rigid frame. In the embodiment shown the superimposed pad comprises a silicone material having, for example, a Shore A durometer of approximately 50 (while other materials and hardnesses are contemplated). Preferably, the faces of the superimposed pad are likewise of a generally outwardly and upwardly concave configuration. It will be understood that the superimposed pad is a elastic material that is configured to elastically deform upon operable positioning within the mouth of a patient, or upon relative movement of the first and second lower extensions, whereas the lower extensions may be a material which surface is difficult to indent (but which can rotate and translate relative to the rest of the frame).

With reference to FIG. 7, the opposing tines are canted such that the peak regions 65, are closer to each other at the bottom end than at the top end, and that the respective inclined surfaces are closer to each other at the bottom end than at the top end. In this manner the faces extend below the widest point of the tooth of a patient (and apply force directly thereon). This limits the ability of the matrix ring to move toward the occlusal surface and slip off. Additionally, the opposing tines are also canted upwardly and inwardly toward the center of the ring such that when separated a distance corresponding to the contact with the teeth, the exposed faces 74, 84 of the lower extensions 52, 54 as well as the front contact surface 92, 94 of the superimposed pad and the central wedge engage.

In operation, the dental professional first selects an appropriately sized and shaped matrix ring. It is contemplated that a single matrix ring will generally be suitable for a majority of the population, however, it is also contemplated that a kit may be provided having a plurality of matrix rings, each of which is provided in a different size to correspond to a number of differently sized teeth and relative mouth dimensions. Once selected the dental practitioner or dentist (hereinafter dental professional) installs a matrix band against the tooth that is to be restored. A number of different matrix bands are available commercially, and the present invention is not limited to any particular type of matrix band or configuration of matrix band.

Once positioned, the dental professional next inserts a wedge into the interproximal space, if desired. Subsequently, the dental professional expands the biasing ring, typically with a pair of expanding jaw pliers. Specifically, the dental professional grasps opposing sides of the ring away from the tines and engages the pliers to separate the opposing tines from each other.

Once the opposing tines have been separated to an extent that the tines can extend on opposing sides of the tooth to be restored and the adjacent tooth, the dental implement is installed into the mouth of the patient. The opposing tines are positioned so that the peak 65 of the central ridge 50 extends into the interproximal space between two adjacent teeth, and so that the bottom end of the base is at or near the gum line. The pliers are then released, so as to gently release the opposing tines onto the adjacent teeth. As the tines may contact with the teeth, the exposed faces 74, 84 of the lower extensions 52, 54 as well as the front contact surface 92, 94 of the superimposed pad and the central wedge engage.

The lower leg extensions of the frame due to their elongated configuration, have the ability to twist, pivot, translate and or rotate relative to the rest of the frame and relative to each other. As such, they provide a generally rigid framework that is nevertheless capable of adaptation to particular tooth anatomy. Additionally, due to the configuration of the exposed faces of the lower extensions, and their inclined configurations, the lower extensions function as spade-like barbs that drive themselves subgingivally where they can engage the undercut region. The spaced apart configuration of these extensions further allows them to function relatively independent of each other. Furthermore, these spade-like barbs provide a positive stop, so as to ensure that the tines do not extend too far interproximally. Additionally in the case of wide embrasures, the lower extensions prevent the tines from entering the proximal box and caving in the matrix band.

Further release of the matrix ring from the pliers, further directs the central wedge into the desired position within the interproximal zone. Additionally the front contact surface of the superimposed pad is then directed into contact with the matrix band and/or the tooth surface. The relatively soft material from which the superimposed pad is made allows for uniform engagement and the uniformity of force application on the tooth and/or matrix band across the superimposed pad.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A matrix ring comprising:
a biasing ring having a substantially hoop-like configuration terminating at two opposing ends which are spaced apart from each other a distance; and
a pair of opposing tines extending inwardly from each of the two ends of the biasing ring toward each other and at least one of the opposing tines further including:
a frame body having a front defined by a central ridge, a first lower extension extending from a first side of the central ridge, and a second lower extension extending from a second side of the central ridge, the first lower extension having a top surface and a bottom surface terminating at an exposed face, the top surface and bottom surface cooperating to define a thickness that reduces toward the exposed face, wherein a portion of the first lower extension proximate the exposed face is configured to rotate and translate relative to the remainder of the frame body upon application of an operable positioning within a mouth of a patient, the second lower extension having a top surface and a bottom surface terminating at an exposed face, the top surface and bottom surface cooperating to define a thickness that reduces toward the exposed face, wherein a portion of the second lower extension proximate the exposed face is configured to rotate and translate relative to the remainder of the frame body upon operable positioning within a mouth of a patient, with the exposed faces of each of the first and second lower extensions being spaced apart from each other and configured for independent relative movement; and
a superimposed pad positioned over a portion of the front of the frame body the superimposed pad having a first side and a second side, the first side extending over the top surface of the first lower extension, the second side extending over the top surface of the second lower extension, the superimposed pad having a first front face and a second front face, which together with the exposed faces of the first and second lower extensions defines the tooth engagement surface of the tine, the superimposed pad comprising a resilient material configured to elastically deform upon operable positioning within the mouth of a patient, or upon relative movement of the first and second lower extensions.

2. The matrix ring of claim 1 wherein the second tine is a substantial mirror image of the first tine about an axis that is positioned substantially midway between the opposing ends of the biasing ring.

3. The matrix ring of claim 2 wherein the first and second front faces of each of the superimposed pads of each of the first and second tines are outwardly and upwardly concave.

4. The matrix ring of claim 2 wherein the exposed face of the first lower extension further includes an inclined face relative to the bottom surface of the first lower extension having an upper edge and a lower edge, with a projecting edge spaced apart from the upper edge, the projecting edge extending further toward the opposing tine than the remainder of the exposed face.

5. The matrix ring of claim 4 wherein the exposed face of the second lower extension further includes an inclined face relative to the bottom surface of the second lower extension having an upper edge and a lower edge, with a projecting edge spaced apart from the upper edge, the projecting edge extending further toward the opposing tine than the remainder of the exposed face.

6. The matrix ring of claim 5 wherein the inclined face of the first and second lower extensions is configured to rotate relative to the remainder of the frame body at least 10° of rotation in either direction about an axis that extends through the respective exposed face.

7. The matrix ring of claim 5 wherein the projecting edge of each of the exposed faces of the first and second lower extensions correspond to the respective lower edge thereof.

8. The matrix ring of claim 5 wherein the exposed face of each of the first and second lower extension is spaced apart from the front face of the respective superimposed pad so as to define a projecting edge therebetween.

9. The matrix ring of claim 5 wherein the superimposed pad comprises a silicone, and the frame body comprises a stainless steel spring wire.

10. The matrix ring of claim 5 wherein the central ridge is outwardly concave between an upper and lower end thereof, while being transversely convex.

11. The matrix ring of claim 2 wherein the inclined face of the first lower extension is inclined at an angle of between 25° and 75° relative to the bottom surface of the first lower extension.

12. The matrix ring of claim 2 wherein the superimposed pad includes at least one crossover portion extending through the central ridge that links the superimposed pad on either side of the central ridge.

13. The matrix ring of claim 12 wherein a pair of spaced apart crossover portions extend through the central ridge linking the superimposed pad on either side of the central ridge.

14. The matrix ring of claim 1 wherein the top surface and the bottom surface of the first lower extension is substantially continuous with the space therebetween tapering toward the exposed face.

15. The matrix ring of claim 1 wherein the opposing ends of the biasing ring terminate within opposing cavities of the respective opposing tines.

16. The matrix ring of claim 1 wherein the central ridge includes an exposed face having a peak, a first side and a second side on an opposite side of the peak from the first side, the first side being substantially continuous with the first surface of the superimposed pad and the second side being substantially continuous with the second surface of the superimposed pad, such that the exposed face of the central ridge also defines a portion of the tooth engagement portion of the tine.

\* \* \* \* \*